US006835362B1

(12) United States Patent
Eriksson

(10) Patent No.: US 6,835,362 B1
(45) Date of Patent: Dec. 28, 2004

(54) CONNECTOR ASSEMBLY

(75) Inventor: Jan-Olof Eriksson, Falkenberg (SE)

(73) Assignee: Getinge Sterilization Aktiebolag, Getinge (SE)

( * ) Notice: Subject to any disclaimer, the term of this patent is extended or adjusted under 35 U.S.C. 154(b) by 435 days.

(21) Appl. No.: 09/979,076

(22) PCT Filed: Jun. 9, 2000

(86) PCT No.: PCT/SE00/01200

§ 371 (c)(1),
(2), (4) Date: Nov. 16, 2001

(87) PCT Pub. No.: WO00/74735

PCT Pub. Date: Dec. 14, 2000

(30) Foreign Application Priority Data

Jun. 9, 1999 (SE) .............................................. 9902152

(51) Int. Cl.[7] ........................... A61L 2/00; B65D 65/00; F17C 1/00; B65B 1/04; F16L 39/00
(52) U.S. Cl. ....................... 422/300; 422/292; 422/302; 422/261; 422/1; 422/26; 422/32; 422/40; 206/435; 220/581; 220/601; 138/89; 141/85; 141/98; 141/285; 285/131.1; 285/132.1; 285/DIG. 901
(58) Field of Search ................................ 422/292, 297, 422/300, 302, 305–307, 25, 40, 294, 38, 1, 5, 26, 28, 32, 261; 206/435; 220/581, 601; 138/89; 141/85, 98, 285; 285/131.1, 132.1, DIG. 901

(56) References Cited

U.S. PATENT DOCUMENTS 5,330,450 A * 7/1994 Lopez ......................... 604/533
6,030,578 A * 2/2000 McDonald .................... 422/24

FOREIGN PATENT DOCUMENTS

EP 0 450 700 A1 10/1991
EP 0 586 307 b1 3/1994

* cited by examiner

Primary Examiner—Robert J. Warden, Sr.
Assistant Examiner—Monzer R. Chorbaji
(74) Attorney, Agent, or Firm—Burns, Doane, Swecker & Mathis, LLP

(57) ABSTRACT

The present invention relates to a connector assembly (3) for connection to a container (1) for sterilising goods, preferably for pharmaceutical applications, and a releasable connector port (5) for releasably connecting said connector assembly (3) to a treatment station (1) for the goods that is contained in said container (1). Said connector assembly (3) further includes a second port that initially is provided with a detachable rapid transfer port cap (4), which cap (4) corresponds to a rapid transfer port means (15) that is provided at a goods transfer station (12). The connector port (5) and the rapid transfer port cap (4) are in fluid connection via a good stopper means (7). The invention also relates to a multi-treatment sterilising system and to a method for transferring sterilised goods from a multi-purpose container using a system according to the invention.

20 Claims, 3 Drawing Sheets

CONNECTOR ASSEMBLY

TECHNICAL FIELD OF THE INVENTION

The present invention relates to a connector assembly including an end portion for connection to a sterilisation container. The connector assembly includes a releasable connector port for releasably connecting said container assembly to a treatment station for multi-purpose treatment of goods, such as plugs, that is enclosed in said container.

The invention also relates to a multi-treatment sterilising system, including a multi-purpose container for treatment and storing of articles being enclosed there within. Finally, the invention relates to a method for transferring sterilised goods from a multi-purpose container using a system according to the invention.

BACKGROUND ART

When sterilising small articles, such as plugs or caps for pharmaceutical purposes, it is known to use a multi-purpose container, in which the articles are submitted to several different treatments such as washing; sterilising and drying. Rubber plugs are usually also siliconised, all within the same multi-purpose container. Siliconising is a procedure for providing the plugs with a thin layer of silicon oil, which makes the introduction of the plugs into pharmaceutical test tubes easier.

After treating the goods in the container, it is desirable to store said container in a manner such that the risk for contamination of the sterilised goods is eliminated. In order to achieve this, the container is pressurised before storing so that the internal pressure of the container is greater than the ambient pressure.

After storing, the goods are to:r be transferred to suitable packages. This must be done in a sufficiently clean environment, such as a clean room or isolator. A problem occur however in keeping the environment clean when it is confronted with the container that has been stored under unclean conditions. To avoid this problem, the exterior of a port of the container has to be sterilised before transfer of the goods into the clean environment through said opening. The procedure for sterilising the port is however time-consuming and difficult to handle. There is also a risk that an un-sterilised port may be inserted into the clean room by mistake, since there is no way to immediately determine whether said port is clean or not.

SUMMARY OF THE INVENTION

The aim of this invention is to eliminate the above mentioned problems during transfer of the sterilised goods to a clean environment. The aim is also to provide a sterilising system where these problems do not occur, and which operates quickly and safely. Additionally, the aim is to provide a method using such a system.

The first of the above mentioned aims is reached by a connector assembly according to the introduction in which said connector assembly further includes a second port that is initially provided with a detachable rapid transfer port cap that corresponds to a rapid transfer port means in a transfer station. The connector port and the transfer port are in fluid connection via a goods stopper means. Said goods stopper means prevents the goods from passing through the connector port when said cap and said means are interconnected for transfer of the goods via the second port to the transfer station.

With goods stopper means we here refer to a means which stops goods from passing through it, but allow fluid to pass through. Such a means could for example be a perforated plate, even though many other designs are possible.

With rapid transfer port cap we do here refer to one of the double doors used in rapid transfer ports such as described in for example EP 0 586 307, SNE LA CALHENE. These kinds of ports consist of a rapid transfer port means, comprising a door and a doorframe that is to be arranged at a clean room wall. The door is inter-connectable with a rapid transfer port cap that seals a container containing the clean goods. When interlocking, one side of the rapid transfer port cap that has been directed outwards from the container and thus could have been contaminated during storing, is locked together with the outer side of the door of the rapid transfer port means. The "double door" comprising the interlocked door and cap can then be opened, while substantially all contamination is safely held between the cap and the door.

According to the invention, there is a connector port assembly comprising one connector port for connection to a treatment station. This connector port can be designed as the ports used in prior art. There is also second port that initially is covered by a detachable transfer port cap. This port will later be used as a transfer port when the cap has been removed and the goods are to be transferred to a clean environment outside of the container. The use of a rapid transfer port thus eliminates the need of sterilising a port of the container for transfer of the sterilised goods.

Performing sterilisation of a port according to prior art takes about 30–40 minutes, while the interconnection and opening of the rapid transfer port takes only about 5–10 minutes. A connector assembly according to the invention thus makes the transfer procedure much more time efficient than the procedures according to prior art.

The function of the goods stopper means is as follows. When the container is connected to the treatment station via the connector port, the transfer port and thus the inside of the rapid transfer port cap will be sterilised as well as the goods inside of the container, since the goods stopper means provide fluid contact between the connector port, where the sterilising medium is supplied, and the rapid transfer port cap.

At a later stage, when the sterilised goods are to be transferred to a clean room for for example packaging, the container is directed so that the rapid transfer port cap is aligned essentially vertically. After removal of the transfer port cap, the goods will flow down through the rapid transfer port opening. Because of the stopper means, no articles will fall in to the dead end of the connector port.

Preferably, said rapid transfer port cap is arranged adjacent to the connector port. This will make the procedure when using and manufacturing the connector assembly considerably easier.

Said connector assembly could advantageously be essentially Y-shaped, with the connector port and the rapid transfer port cap being provided at the arms of the Y, respectively. The base of the Y-shaped connector assembly is constituted by an end portion for connection with the container. In such an embodiment, the different ports are easily handled, since changing between the ports can be made simply by rotation of the connector means and/or the container.

Preferably the connector assembly is provided at an end of the container, that is directed upwardly during treatment and downwards during transfer of the content in said container. During treatment, when the connector assembly is directed upwards, no liquids or fluids can be stored in the connector assembly. During transfer, the connector assembly, or at least the rapid port cap should be directed downwards to empty the container merely by help of gravity.

The connector assembly is advantageously provided with a sensor for detecting the presence of the rapid transfer port cap on said container. If the sensor shows that no rapid transfer port cap is present, the sterilisation process would not continue. The sensor provides thus an easy control device to ensure that the treatment process of the goods is performed properly.

The invention further relates to a multi-treatment sterilising system, including a multi-purpose container for treatment and storing of articles being enclosed there within, at least one treatment station, a transport means and a transfer station for transferring said objects into a clean area for further processing such as packing, and being characterised in said system including a connector assembly according to the invention, which assembly is arranged at the container.

Preferably said transfer station includes rapid transfer port means corresponding to the rapid transfer port cap of the connector assembly. The transfer station could also be provided with glove ports for manually interconnecting the rapid transfer port means and the rapid transfer port cap for detachment of said rapid transfer port cap from said container. The process of interconnecting the rapid transfer port cap with the rapid transfer port means to form the double port, which contains any eventual contamination, is so delicate with ports available today, that it can only be made by hand. Therefore, glove ports are necessary to allow manual interconnecting of the means and cap.

Advantageously, said transfer station can be provided with a feed pipe that is pivotably arranged to be movable from a position away from the container to a position extending through the opened rapid transfer port of the container. When the rapid transfer port is open, i. e. the cap and means are interconnected, there is still a small risk of contamination from the sides of the doorframe in which the door was initially disposed. To avoid spreading of this contamination to the sterilised goods, the feeding pipe can be inserted through the opening of the rapid transfer port and thus provide a clean outlet channel for the sterilised goods in the container.

Finally the invention also relates to a method for transferring sterilised goods from a multi-purpose container using a system according to the invention. The rapid transfer port cap of the connector assembly and the rapid transfer port means of the transfer station are then manually interconnected to remove said cap from the container, using glove ports for manually handling the means and cap.

DETAILED DESCRIPTION OF PREFERRED EMBODIMENTS OF THE INVENTION

Figure 1:
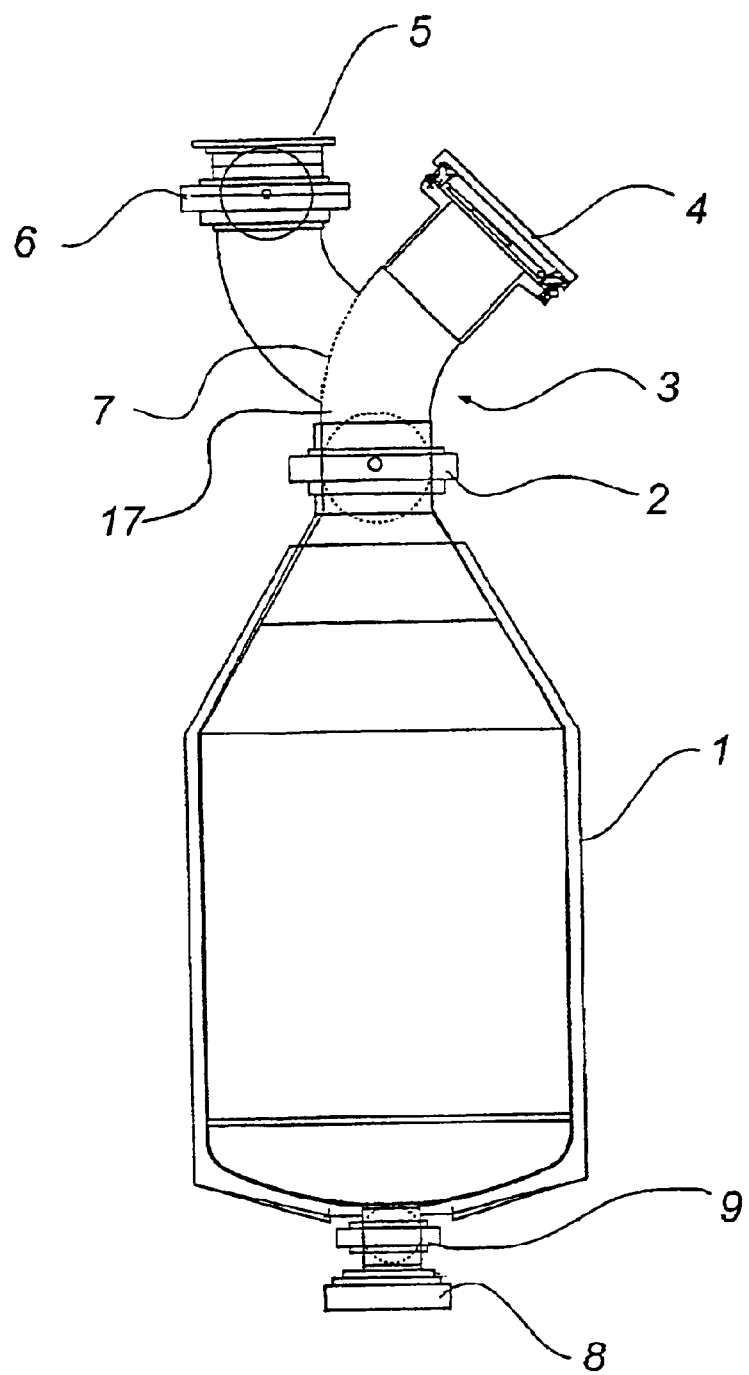
FIG. 1 is a side view of an embodiment of a connector assembly according to the invention being connected to a multi-purpose sterilisation container

FIG. 1 shows a multi-purpose double-walled container 1 according to prior art. The container 1 has an essentially cylindrical shape that narrows conically towards a first throttle valve 2. At the throttle valve 2 a connector assembly 3 according to the invention is connected to the container 1 via an end portion 17. The connector assembly 3 is essentially Y-shaped, with the base of the Y forming the end portion 17 which is connected to the first throttle valve 2. The first of the arms of the Y (here the right hand side) is at its end provided with a rapid transfer port cap 4, which initially seals the first arm of the connector assembly 3 The end of the second arm of the Y-shaped connector assembly 3 is provided with a connector port 5. The second arm is also provided with a second throttle valve 6. A perforated wall 7 is provided between the arms of the Y-shaped connector assembly 3.

The wide base end of the container is provided with a bottom port 8 and a corresponding throttle valve 9, according to prior art.

Figure 2:
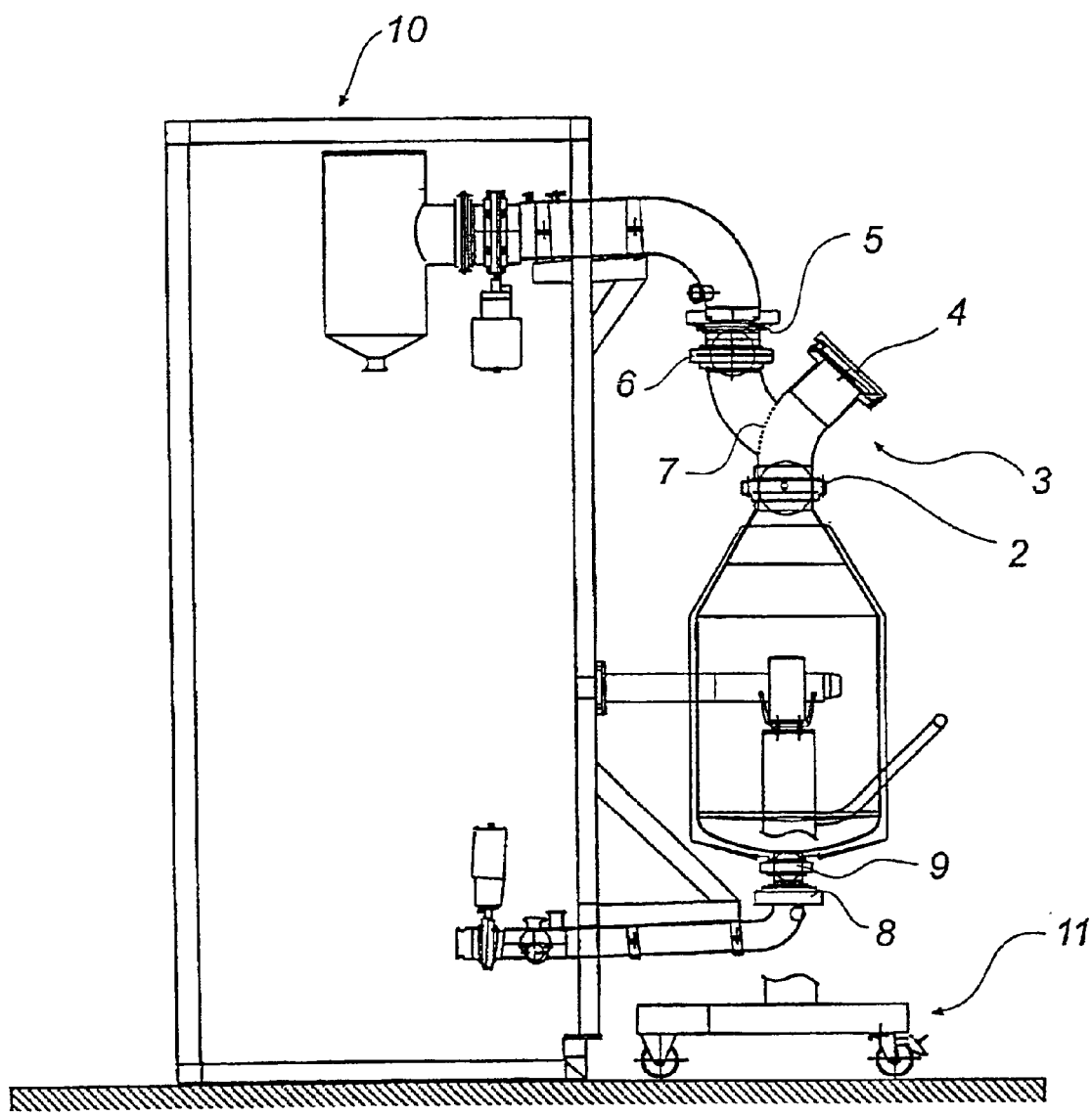
FIG. 2 is a side view of the connector assembly and sterilisation container of FIG. 1 being connected to a treatment station.

In FIG. 2 the Y-shaped connector assembly 3 and container 1 of FIG. 1 is shown as connected to a treatment station 10. The container 1 is filled with the goods to be sterilised, for example plugs or caps used for pharmaceutical applications. The connector port 5 on one arm of the connector assembly 3 is connected to a first opening of the treatment station 10, whereas the rapid transfer port cap 4 is sealing the other, free arm of the Y-shaped connector assembly 3. The bottom connector port 8 is connected to a second opening of the treatment station 10, in a similar way as the connector port 5. Adjacent to the bottom connector port 6 there is a throttle valve 9.

The treatment station 10 can be arranged to perform several different operations to the goods in the container 1, such as washing, sterilising, siliconising and drying them. The last mentioned procedures are particularly important when treating plugs for use in for example pharmaceutical test tubes. During the different operations of the treatment station 10, the three throttle valves 6, 2, and 9 can be opened and closed as necessary for the particular operation. One should note that, provided the throttle valve 6 is open, the rapid transfer port cap 4 is in fluid contact with the connector port 5 via the perforations in perforated wall 7, and thus to the treatment station 10. The arm of the connector assembly 3 containing the rapid transfer port cap 4, as well as the port cap 4 itself will thus be sterilised during the operation of the treatment station 10.

Preferably the location of the rapid transfer port cap 4 will be automatically controlled by a sensor (not shown) to ensure its presence at the arm before continuing with the treatment of the goods. The throttle valves 6, 2, and 9 will first be opened and can then be controlled automatically by a control station that performs a chosen operation program.

The last steps in the procedure performed when the container 1 and connector assembly 3 are disposed in the treatment station 10 are that the container 1 and connector assembly 3 are pressurised, and the outer throttle valves 6, 9 are closed. The container 1 and connector assembly 3 can then be released from the treatment station 10 and preferably brought to a transport station 11, for storing or for transport to a transfer station. The pressure inside the container 1 and connector assembly 3 is now higher than the ambient air pressure, which serves to prevent that any contamination will enter the container 1 when stored.

Figure 3:
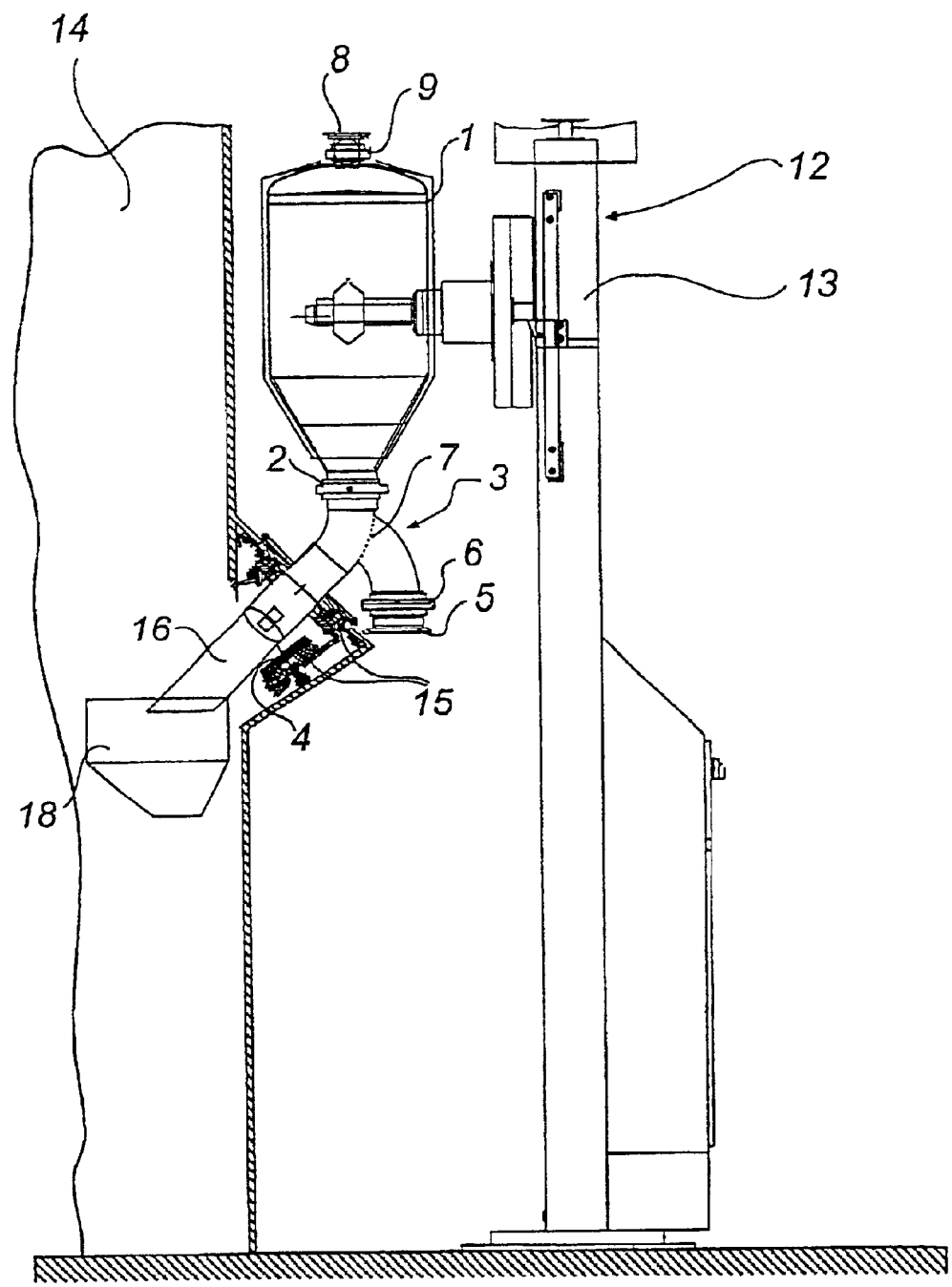
FIG. 3 is a side view of the connector assembly and sterilisation container of FIG. 1 being connected to a transfer station.

In FIG. 3, the container 1 and connector assembly 3 is shown when connected to a transfer station 12. The transfer station 12 consists of a lift and turn station 13, which lifts the container 1 and connector assembly 3 up from the transport means 11 to a comfortable height, and turns the container 1

180 degrees, so that the connector assembly 3 will be directed downwards. The transfer station 12 comprises also a clean room 14, in which specific conditions of minimum contamination must be withheld. Inside the clean room 14, a retainer 18, for example a hopper, is arranged to receive the sterilised articles that are initially contained in the container 1. The clean room 14 wall is provided with a rapid transfer port means 15 corresponding to the rapid transfer port cap 4 of the connector assembly 3. Further, the clean room 14 is provided with glove ports (not shown) through which the rapid transfer port means 15 and the cap 4 can be manually interconnected and the double port thus formed be opened. The clean room 14 is also provided with a pivotable feeding pipe 16, that can be pivoted to fit between connector assembly 3 of the container 1 and the retainer 13. After opening the double port and inserting the feeding pipe 16, the throttle valve 2 can be opened and the sterilised goods let out through the rapid transfer port opening and down the feeding pipe 16 into the hopper 18. Thanks to the stopper means 7, no articles will fall through the first arm of the Y and end up in the dead end at the throttle valve 6.

A container 1 that has been stored could advantageously be provided with a pressure sensor device, indicating the pressure inside the container 1. If the pressure is the same as when the container was stored, it will ensure that no contamination of the contents has occurred during storing.

Many different embodiments apart from the one being described here above can be made in the scope of the invention. For example the connector assembly 3 must not be formed as an Y, but could have any other shape suitable for three openings, like for example a U- or T-shape. The goods stopper means 7 could instead of a perforated wall be made by some kind of net or grid, letting fluids pass through it, but not the goods to be sterilised. Hence, the mesh size or the distance between the hindering parts of the stopper means 7 must be smaller than the objects to be sterilised.

What is claimed is:

1. A connector assembly comprising:
   an end portion for connection to a sterilisation container for sterilising goods, such as plugs or caps;
   a releasable connector port for releasably connecting said connector assembly to a treatment station for multi-purpose treatment of the goods that is enclosed in said sterilisation container; and
   a second port that initially is provided with a detachable rapid transfer port cap, said rapid transfer port cap corresponds to a rapid transfer port means that is provided at a goods transfer station, wherein the connector port and the rapid transfer port cap are in fluid connection via a goods stopper means, said goods stopper means preventing the goods from passing through said connector port when said rapid transfer port cap and said rapid transfer port means are interconnected for transfer of the goods via the second port to the goods transfer station.

2. A connector assembly according to claim 1, wherein said rapid transfer port cap is arranged adjacent to the connector port.

3. A connector assembly according to claim 2, wherein said connector assembly is essentially Y-shaped, with the connector port and the rapid transfer port cap being provided at the arms of the Y, respectively.

4. A connector assembly according to claim 2, wherein the connector assembly is provided at an end of the sterilisation container, that is means to be directed upwardly during treatment and downwards during transfer of the content in said sterilisation container.

5. Connector assembly according to claim 2, wherein said connector assembly is provided with a sensor for detecting the presence of said rapid transfer port cap on said sterilisation container.

6. A connector assembly according to claim 1, wherein said connector assembly is essentially Y-shaped, with the connector port and the rapid transfer port cap being provided at the arms of the Y, respectively.

7. A connector assembly according to claim 6, wherein a base of the Y-shaped connector assembly is connected to the sterilisation container.

8. A connector assembly according to claim 7, wherein the connector assembly is provided at an end of the sterilisation container, that is means to be directed upwardly during treatment and downwards during transfer of the content in said sterilisation container.

9. A connector assembly according to claims 6, wherein the connector assembly is provided at an end of the sterilisation container, that is means to be directed upwardly during treatment and downwards during transfer of the content in said sterilisation container.

10. Connector assembly according to claim 6, wherein said connector assembly is provided with a sensor for detecting the presence of said rapid transfer port cap on said sterilisation container.

11. A connector assembly according to claim 1, wherein the connector assembly is provided at an end of the sterilisation container, that is means to be directed upwardly during treatment and downwards during transfer of the content in said sterilisation container.

12. A connector assembly according to claim 1, wherein said connector assembly is provided with a sensor for detecting the presence of said rapid transfer port cap on said sterilisation container.

13. Method for transferring sterilised goods from a multi-purpose container using a system according to claim 12 wherein the rapid transfer port cap of the connector assembly and the rapid transfer port means of the transfer station are manually interconnected to remove said rapid transfer port cap from the multi-purpose container, using glove ports for manually handling the rapid transfer port means and rapid transfer port cap.

14. Multi-treatment sterilizing system, including a multi-purpose container for treatment and storing of goods being enclosed there within, at least one treatment station, a transport means and a transfer station for transferring said goods into a clean area for further processing such as packing, said system including a connector assembly according to claim 1, which connector assembly is arranged at the multi-purpose container.

15. Multi-treatment sterilizing system according to claim 14, wherein said transfer station includes rapid transfer port means corresponding to the rapid transfer port cap of the connector assembly, and is provided with glove ports for manually interconnecting the rapid transfer port means and the rapid transfer port cap for detachment of said rapid transfer port cap from said multi-purpose container.

16. Multi-treatment sterilising system according to claim 15, wherein said transfer station being provided with a feeding pipe that is pivotably arranged to be movable from a position away from the multi-purpose container to a position extending through the opened rapid transfer port of the multi-purpose container and into the clean area.

17. Method for transferring sterilised goods from a multi-purpose container using a system according to claim 15 wherein the rapid transfer port cap of the connector assembly and the rapid transfer port means of the transfer station are manually interconnected to remove said rapid transfer port cap from the multi-purpose container, using glove ports for manually handling the rapid transfer port means and rapid transfer port cap.

18. Multi-treatment sterilising system according to claim 14, wherein said transfer station being provided with a feeding pipe that is pivotably arranged to be movable from a position away from the multi-purpose container to a position extending through the opened rapid transfer port of the multi-purpose container and into the clean area.

19. Method for transferring sterilised goods from a multi-purpose container using a system according to claim 18 wherein the rapid transfer port cap of the connector assembly and the rapid transfer port means of the transfer station are manually interconnected to remove said rapid transfer port cap from the multi-purpose container, using glove ports for manually handling the rapid transfer port means and rapid transfer port cap.

20. Method for transferring sterilised goods from a multi-purpose container using a system according to claim 14 wherein the rapid transfer port cap of the connector assembly and the rapid transfer port means of the transfer station are manually interconnected to remove said rapid transfer port cap from the multi-purpose container, using glove ports for manually handling the rapid transfer port means and rapid transfer port cap.

* * * * *